United States Patent [19]

Komis

[11] Patent Number: 4,713,066
[45] Date of Patent: Dec. 15, 1987

[54] EXTERNAL MALE URINARY CATHETER WITH GARMENT

[76] Inventor: Glenna Komis, P.O. Box 163, Hammonton, N.J. 08037

[21] Appl. No.: 841,590

[22] Filed: Mar. 20, 1986

[51] Int. Cl.⁴ .............................................. A61F 5/44
[52] U.S. Cl. ................................. 604/353; 604/349; 604/351
[58] Field of Search ............... 604/317, 319, 322, 326, 604/327, 316, 343–353, 133; 4/144.1–144.4; 2/403, 405

[56] References Cited

U.S. PATENT DOCUMENTS

| | | | |
|---|---|---|---|
| 2,529,999 | 11/1950 | Chambers | 604/351 |
| 2,739,595 | 3/1956 | Huggins | 604/327 |
| 2,745,404 | 5/1956 | Wood-Minor | 604/317 |
| 2,796,864 | 6/1957 | Johnson | 604/347 |
| 3,368,561 | 2/1968 | Ericson et al. | 604/347 |
| 3,421,504 | 1/1969 | Gibbons | 604/349 |
| 3,721,243 | 3/1973 | Hesterman et al. | 604/353 |
| 4,392,858 | 7/1983 | George et al. | 604/133 |
| 4,553,968 | 11/1985 | Komis | 604/353 |

FOREIGN PATENT DOCUMENTS

| | | | |
|---|---|---|---|
| 0119143 | 9/1984 | European Pat. Off. | 604/349 |
| 8000535 | 4/1980 | PCT Int'l Appl. | 604/349 |
| 0637978 | 5/1950 | United Kingdom | 604/351 |

Primary Examiner—C. Fred Rosenbaum
Assistant Examiner—Mario Costantino
Attorney, Agent, or Firm—Dann, Dorfman, Herrell & Skillman

[57] ABSTRACT

An external male urinary catheter, generally in the form of a condom, molded to form accordion pleats running circumferentially of the sheath so as to enable the catheter to be telescopically folded, applied, and then expanded to connect to drainage tubing and further to a compressable collection receptacle in a manner that creates a negative pressure mechanism, the fixed flange of a supporting garment meshed with the corresponding flange of said catheter by a vulcanization process rendering the assembly virtually free of any constriction.

11 Claims, 6 Drawing Figures

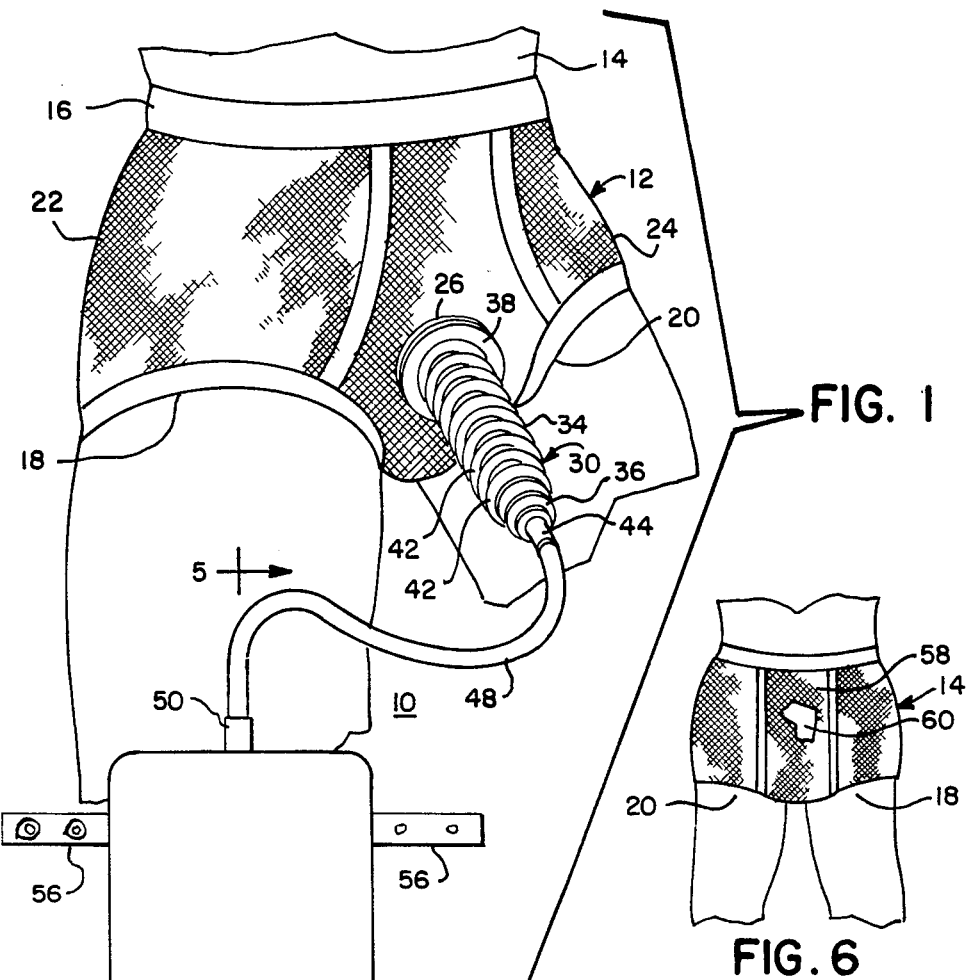
FIG. 1
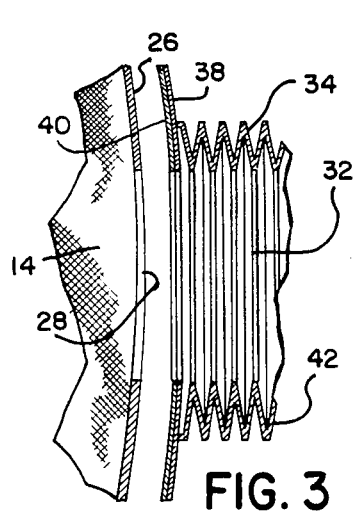
FIG. 6
FIG. 3

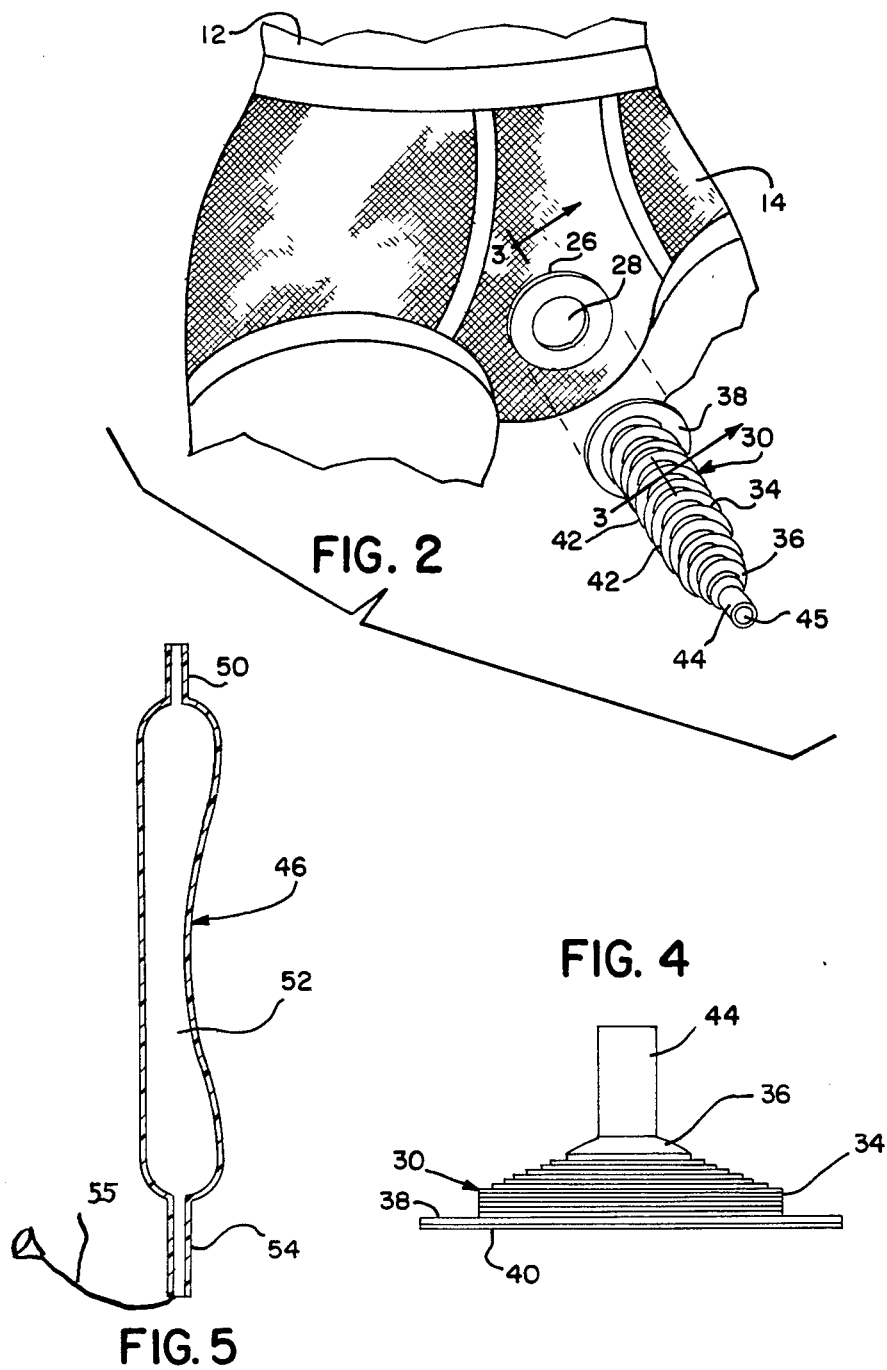

EXTERNAL MALE URINARY CATHETER WITH GARMENT

In my original application, Ser. No. 492,145 filed June 9, 1983, now U.S. Pat. No. 4,553,968, granted Nov. 19, 1985 and entitled "External Male Urinary Catheter With Garment", there is disclosed an exdwelling catheter supported by a garment of the men's brief type. The garment has right and left leg openings, side panels attached to a waistband, and a frontal opening positioned to register with the penis of the male wearer. Strands of the absorbent, porous garment and its cylindrical extension are meshed with the flange of a rubber external male urinary catheter by a vulcanization process.

The effectiveness of the said invention is dependent upon the use of a full men's brief that provides a safe and comfortable support structure where, previously, constricting mechanisms such as adhesive tape, a hard rubber ring, or a tightly-fitting sponge member predisposed the patient to the complications of tissue necrosis, loss of function, obstruction to the flow of urine, urinary tract infection, pain, and general discomfort.

While such a construction has been found quite satisfactory, there has appeared difficulty in the application of the one-piece garment/catheter assembly that cannot be rolled onto the penis as is a conventional condom. The overall object of the present invention is to provide a product which is constructed to be more efficiently and effectively applied and utilized by both health care professionals and laypersons.

Accordingly, the catheter has been modified so that accordion pleats provide a mechanism whereby the catheter can be telescopically folded or compacted along its tubular axis, and then expanded to its functioning state.

Another object of the present invention is to provide a garment comprised of a porous, absorbent, disposable material, with a partially padded back portion lined with a waterproof layer between the padding and the garment panel. As previously disclosed, the desirability of an absorbent, porous material is based on the need for absorption, ventilation, and evaporation of body fluids to preserve the integrity of the skin and to prevent rash, breakdown, and infection. The padding and waterproof lining are now added to the back of the garment for the management of fecal incontinence. While such an embodiment suggests a diaper product, the present invention encourages the flow and containment of urine away from the body, where its byproducts cannot damage the skin.

A further object of this invention is to provide a collection receptacle or leg bag that enhances the gravitational flow of urine. The collection receptacle is attached to the polyethylene drainage tubing and then compressed with its valvular member in an open position. The valvular member is then closed with the collection receptacle still in a compressed state. This manner of attachment creates a negative pressure mechanism that directs the flow of urine downwards.

Finally, an object of the present invention is to provide an external male urinary catheter assembly that a confused or uncooperative patient is less likely to remove by virtue of the more comfortable, more secure design.

These together with other objects and advantages which will become subsequently more apparent reside in the details of construction and operation as more fully hereinafter described and claimed, reference being had to the accompanying drawings forming a part hereof, wherein like numerals refer to the parts throughout.

In the drawings,

FIG. 1 is a perspective view of the present invention, illustrating the method of applied utilization with the external catheter and garment in unison;

FIG. 2 is an exploded perspective view, illustrating the association between the garment and the catheter;

FIG. 3 is a fragmentary section with the catheter in a partially compacted condition emphasizing the nature of attachment of the catheter to the brief;

FIG. 4 depicts the external male urinary catheter in a fully compacted or collapsed position;

FIG. 5 is a section taken on the line 5—5 of FIG. 1 showing the collection receptacle in a compressed state in broken lines; and FIG. 6 is a view of the back of the garment with a part broken away to reveal the padded, lined middle section.

With specific reference to the drawings, an embodiment of the present invention is generally designated by reference numeral 10. The basic features of this invention, as illustrated in FIG. 1, include a supporting garment 12 attached to catheter 30 which is further connected to collection receptacle 46 by polyethylene drainage tubing 48.

Still with reference to FIG. 1, garment 12, comprised of porous, absorbent, disposable material has elasticized right and left leg openings 18 and 20, respectively, and an elasticized waistband 16 at the top, to which are attached right and left panels 22 and 24, respectively. It is understood that flexibility within the overall design of the present invention is maintained to enable adjustment or accommodation to the patient's waist size. Applicant has found that the standard diameter of an ordinary condom, i.e., 40-45 mm, is consistent with the objections of the present invention as stated and further set forth below.

FIG. 2 shows a frontal opening 28 in garment 12 positioned to register with the penis of the male user. Frontal opening 28 has an inside diameter adapted to encircle the penis without causing structural or functional constriction. Fixed flange 26 circumscribes frontal opening 28 and represents treated elastomeric material such that the elastomeric material is meshed with strands of garment 12 by appropriate industrial processes, e.g., vulcanization, heat setting or the like. The meshing is desirable to eliminate the excess bulk associated with previous devices and, at the same time, produce a lighter weight but still effective means of support. Fixed flange 26 which, in turn, is supported by garment 13, then, creates an anchoring mechanism for catheter 30 in lieu of the above-mentioned constricting mechanisms.

Catheter 30, generally in the form of a condom, is also made of treated elastomeric material rendering catheter 30 a moderately thin, flexible, resilient yet durable tubular sheath capable of being molded so as to provide accordion pleats 42 that run circumferentially of the sheath. The body of catheter 30 is formed by alternating inner and outer diameters 32 and 34, respectively.

The diameter of the internal cavity of of the catheter at its proximal end, as determined by the inner diameter 32 and as referred to in FIG. 3, corresponds to that of frontal opening 28. The proximal end of catheter 30 extends to form flange 38 which is attached to fixed flange 26 by adhesive 40 or by appropriate industrial processes so as to provide a continuous interlock that adds firmness to the support structure.

The above-described accordion pleats enable catheter 30, now united with garment 12, to be telescopically folded, as illustrated in FIG. 4, and thereby more easily applied onto the penis. Previously, the one-piece garment/catheter assembly proved to be problematic in its application where the patient was confronted with a dangling, loose catheter member that could not be rolled onto the penis as is a conventional condom.

The distal portion of catheter 30 gradually reduces in internal diameter, as shown in FIGS. 2 and 4, so that the inner diameter of pleats may be snugly engaged by the tip of the penis without constricting the flow of urine therethrough. The catheter is molded with a converging end portion 36 to end in cylindrical tubular member 44. Aperture 45 of tubular member 44, as shown in FIG. 2, has a slightly larger diameter than that of polyethylene drainage tubing 48. Drainage tubing 48 can therefore be fitted into aperture 45 and thus makes possible fluid communication between catheter 30 and collection receptacle 46 at its inlet 50. The outlet 54 of the receptacle 46 is connected to a valve 55.

Collection receptacle 46, now connected to polyethylene drainage tubing 48, is essentially a polyethylene bag which is normally expanded but is capable of being compressed as illustrated in broken lines in FIG. 5. Valvular member 55 is left open as enough pressure is applied to bring together the sides of collection receptacle 46. Valve 55 is then closed. The tendency of the receptacle to expand to its normal shape creates a negative pressure mechanism akin to a siphon. Urine is drawn away from the body as long as collection receptacle 46 remains at a level below the urinary bladder. Urine collected in the receptacle is eliminated through tubular outlet member 54 and valve 55.

Polyethylene drainage tubing 48 should be taped to the patient's thigh to prevent pull on the device and consequent pain and discomfort. Collection receptacle 46 has means to be attached by strap 56 to the ambulatory wearer at his calf or to the bedside of the bedridden patient.

While the above description contains many specifities, these should not be construed as limitations on the scope of the invention, but, rather, as an exemplification of one preferred embodiment thereof. For example, the material of the garment may not necessarily be disposable after one-time use. In that case, the garment along with the catheter would be conveniently laundered and reused. Or, the garment may be composed of washable and reusable fabric with the catheter being detachable and disposable after one-time use. Here, adhesive would be reapplied onto both flanges. Accordingly, the scope of the invention should be determined not by the embodiment illustrated, but by the appended claims and their legal equivalents.

I claim:

1. An external male urinary catheter assembly comprising a moderately thin, flexible, resilient durable tubular sheath dimensioned to be positioned in enclosing relation to a substantial portion of the penis, said sheath including a distal tubular member having a central aperture providing an open end, the proximal end of said sheath opposite to said distal end portion forming an annular flange, said catheter sheath having a pleated portion between said distal and proximal ends, at the proximal end said pleats having an inner diameter to encircle the penis without constricting the same and at the distal end said pleats having an inner diameter smaller than the inner diameter at the proximate end, and a resilience to snugly engage the tip of the penis without constricting the flow of urine therethrough; drainage tubing telescopically engaging said tubular member to communicate at the distal end with said tubular sheath through said aperture and extending to a connection element, said connection element communicating with a collection receptacle having means for attachment either to the ambulatory wearer at his calf or to the bedside of the bedridden wearer; and a supporting garment of the men's brief type, having elasticized leg openings and an elasticized waistband, said garment composed of an absorbent material and having an annular reinforcement on the front thereof complementary to said flange, and dimensioned to encircle the penis without constricting the same, said flanged end portion engaging said reinforcement and securely united thereto by fastening means continuously circumscribing said reinforcement and said flange respectively to provide a continuous connection therebetween without substantially constricting the penis.

2. An external male catheter assembly according to claim 1 wherein said collection receptacle is a hollow member having a normally-expanded cavity, the receptacle being a polyethylene bag capable of being compressed by bringing the sides together, a valve for said receptacle operable between open and closed positions to be open to permit collapse of said cavity from its normally-expanded condition to its compressed condition, and to close off said cavity when the bag is in its compressed condition, the bag being connected fluid-tight to said drainage tubing so that the tendency of the bag to return to its normal shape creates a negative pressure in its cavity and said drainage tubing.

3. A catheter assembly according to claim 1 wherein said pleats are accordion pleats which afford compacting of said sheath along its tubular axis for ease of application to the penis.

4. A catheter assembly according to claim 1 wherein a selected number of the pleats adjacent the proximal end have the same inner diameter to produce a generally cylindrical tubular interior in the sheath, and the remaining pleats toward the distal end have diminishing inner diameters to provide an interior diameter in the sheath which generally tapers toward said tubular connection element.

5. A catheter assembly according to claim 1 wherein said supporting garment comprises two side panels, a front panel and a rear panel, said front panel having said frontal opening therein in a position to register with the penis of the wearer, and said rear panel having padding and a waterproof lining between the padding and the panel in a position to register with the anal opening of the wearer.

6. A catheter assembly according to claim 1 wherein said fastening means comprises a layer of adhesive between said reinforcement and said flange to firmly interconnect the same.

7. A catheter assembly according to claim 6 wherein said adhesive layer is releasable to afford replacement of the catheter after use.

8. An external urinary catheter for use by male patients in assembly with drainage tubing extending to a collection receptacle adapted to be attached to an ambulatory wearer at his calf or to the bedside of the bedridden wearer, said catheter comprising a supporting garment of porous absorbent material having front and rear panels connected together to snugly encircle the trunk of the male patient, said garment having en elasticized waist band and elasticized leg openings to retain the garment in place, the front panel having a frontal opening and an annular reinforcement surrounding the frontal opening, having a diameter adapted to encircle the penis of the male patient without constricting the same, said catheter further comprising a moderately thin, flexible, resilient, durable tubular sheath, dimensioned to fit in enclosing relation to a substantial portion of the penis, the tubular sheath having a diameter and resilience snugly engaging the outer circumference of the penis without constricting the flow of urine through the same, said sheath having a flange portion at its proximal end engaging said annular reinforcement and securely united therewith continuously about the entire circumference of the flange portion and the annular reinforcement to provide a continuous connection without substantially constricting the penis, said sheath including at its distal end at a distance to be positioned beyond the tip of the penis, a tubular open end member telescopically connected to said drainage tubing, said sheath having circumferential pleats between said proximal and distal ends, the inner diameter of the pleats at the proximal end corresponding to the diameter of said frontal opening, and being smaller at the distal end to provide said snug engagement of the outer circumference of the penis adjacent its tip.

9. A catheter according to claim 8 wherein a first series of said pleats adjoining the proximal end of said sheath all have inner edges of the same diameter to define a generally cylindrical passage communicating with said frontal opening, and a second series of said pleats from said first series toward the distal end of said sheath having inner edges of decreasing diameter to define a tapering passage terminating in said open tubular end.

10. A catheter according to claim 9 including a conveying end portion between said second series of pleats and said open tubular end.

11. A catheter according to claim 9 wherein said pleats afford compaction of said sheath along its tubular axis to facilitate engagement of the penis within the inner diameter of said pleats.

* * * * *